(12) United States Patent
Tanaka (10) Patent No.: US 8,639,149 B2
(45) Date of Patent: Jan. 28, 2014

(54) IMAGE FORMING APPARATUS INCLUDING FILTER SUBSTANTIALLY PARALLEL TO VENTILATION DIRECTION OF EXHAUST DUCT

(75) Inventor: Gakushi Tanaka, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 368 days.

(21) Appl. No.: 12/929,518

(22) Filed: Jan. 31, 2011

(65) Prior Publication Data

US 2011/0200494 A1 Aug. 18, 2011

(30) Foreign Application Priority Data

Feb. 12, 2010 (JP) ................................ 2010-029379

(51) Int. Cl.
*G03G 21/00* (2006.01)

(52) U.S. Cl.
USPC ............................................. 399/93

(58) Field of Classification Search
USPC .................................... 399/92, 93
See application file for complete search history.

(56) References Cited

U.S. PATENT DOCUMENTS

| | | | | |
|---|---|---|---|---|
| 7,486,904 B2 * | 2/2009 | Sato et al. | .......... | 399/92 |
| 8,238,779 B2 * | 8/2012 | Doshoda et al. | .......... | 399/92 |
| 2002/0031367 A1 * | 3/2002 | Yamamoto et al. | .......... | 399/93 |
| 2004/0037582 A1 * | 2/2004 | Shin | .......... | 399/93 |
| 2006/0056874 A1 * | 3/2006 | Kim et al. | .......... | 399/93 |
| 2008/0219695 A1 * | 9/2008 | Doshohda et al. | .......... | 399/93 |

FOREIGN PATENT DOCUMENTS

| | | |
|---|---|---|
| JP | 02297572 A | 12/1990 |
| JP | 03020758 A | 1/1991 |
| JP | 05313456 A | 11/1993 |
| JP | 07-311519 | 11/1995 |
| JP | 09-160451 | 6/1997 |
| JP | 09218620 A | 8/1997 |
| JP | 11167322 A | 6/1999 |
| JP | 2002274668 A | 9/2002 |
| JP | 2002302278 A | 10/2002 |
| JP | 2004341097 A | 12/2004 |
| JP | 2005257768 A | 9/2005 |
| JP | 2006030631 A | 2/2006 |
| JP | 2006119313 A | 5/2006 |
| JP | 2006-220794 | 8/2006 |
| JP | 2006-330565 | 12/2006 |
| JP | 2007-078976 | 3/2007 |
| JP | 2007133272 A | 5/2007 |
| JP | 2007147835 A | 6/2007 |
| JP | 2007171913 A | 7/2007 |
| JP | 2007328115 A | 12/2007 |
| JP | 2010048972 A | 3/2010 |

OTHER PUBLICATIONS

Japanese Office Action mailed Jun. 11, 2013.
Japanese Office Action mailed Sep. 3, 2013.

* cited by examiner

*Primary Examiner* — Sophia S Chen (74) *Attorney, Agent, or Firm* — Harness, Dickey & Pierce, P.L.C.

(57) ABSTRACT

An image forming apparatus includes an exhaust fan, an exhaust duct, and a filter. The exhaust duct is configured to discharge a gas in an apparatus body to the outside thereof by using an airflow generated by the rotation of the exhaust fan. The filter is provided in a pathway of an airflow flowing through the exhaust duct, arranged substantially parallel to a ventilation direction of the exhaust duct, and configured to reduce chemical substances contained in the gas.

14 Claims, 7 Drawing Sheets

IMAGE FORMING APPARATUS INCLUDING FILTER SUBSTANTIALLY PARALLEL TO VENTILATION DIRECTION OF EXHAUST DUCT

CROSS-REFERENCE TO RELATED APPLICATIONS

The present invention claims priority pursuant to 35 U.S.C. §119 from Japanese patent application No. 2010-029379, filed on Feb. 12, 2010 in the Japan Patent Office, which is hereby incorporated by reference herein in its entirety.

BACKGROUND OF THE INVENTION

1. Field of the Invention

The present invention relates to an image forming apparatus, such as a printer and a copier, having a function of discharging a gas generated within the apparatus to the outside thereof.

2. Description of the Related Art

Some image forming apparatuses are provided with an exhaust fan, an exhaust duct, and a filter to reduce or remove an odorous substance volatilized from toner due to the heat generated in a fixing process and/or to reduce or remove ozone generated from a charging unit.

Thus, for example, an activated carbon filter is arranged between the front and rear sides in the ventilation direction to reduce pressure loss in the exhaust duct and provide a beneficial deodorizing effect.

Along with improvement of office environment, odor, for example, has become more noticeable than before, and the reduction thereof has been required. The odorous substance removal efficiency can be increased by providing plural types of filters or filtering capacities. However, the pressure loss in a filter unit is increased in accordance with the number of provided filters. The increase in pressure loss leads to an increase in output of the exhaust fan, and therefore causes an increase in noise and power consumption due to an increase in rotation rate of the fan.

Figure 1:
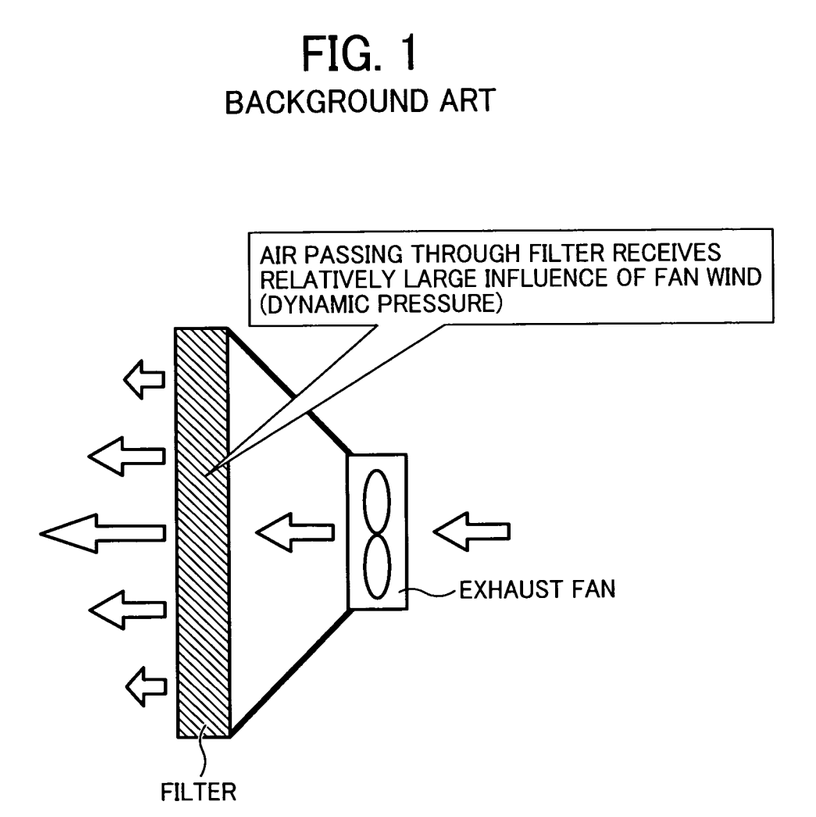
FIG. 1 is a conceptual diagram for explaining the influence of dynamic pressure on air passing through a filter.

According to the above-described background example, the activated carbon filter is arranged between the front and rear sides in the ventilation direction. That is, the filter is arranged perpendicular to the airflow in the exhaust duct. Thus, the configuration is open to improvement in terms of pressure loss. Further, as with another background example illustrated in FIG. 1, if the filter is arranged perpendicular to the ventilation direction of the exhaust duct, the influence of fan wind (i.e., dynamic pressure) generated by the exhaust fan on the air passing through the filter is relatively large, and the wind velocity of the airflow passing through the filter tends to vary due to uneven impact of the wind on the filter. Further still, the generation of odor varies depending on the way the image forming apparatus is used, and moreover the perception of odor is substantially different from person to person.

SUMMARY OF THE INVENTION

The present invention describes a novel image forming apparatus.

In one embodiment, the image forming apparatus includes an exhaust fan, an exhaust duct and a filter. The exhaust duct is configured to discharge a gas in an apparatus body to the outside thereof by using an airflow generated by the rotation of the exhaust fan. The filter is provided in a pathway of an airflow flowing through the exhaust duct and arranged substantially parallel to a ventilation direction of the exhaust duct, and configured to reduce or remove chemical substances contained in the gas.

The area of the filter exposed to the airflow in the pathway may be larger than the cross-sectional area of the exhaust duct.

The filter may be provided in the vicinity of and substantially parallel to an external surface of the apparatus body.

The exhaust duct may include a filter installation portion in which the filter is installed, and which is located outside an external surface of the apparatus body and detachably attachable to the external surface.

An opening of the filter installation portion may have a variable area.

The exhaust duct may include a fixed portion and a movable portion which is movable with respect to the fixed portion, and which is moved to change the opening.

The above-described image forming apparatus may further include a wind rectification rib provided in a pathway space located between the exhaust fan and the filter.

The above-described image forming apparatus may further include a fixing unit provided in the apparatus body. The exhaust duct may include a gas introduction inlet provided in the vicinity of the fixing unit.

The above-described image forming apparatus may further include a process cartridge unit provided in the apparatus body. The exhaust duct may include a gas introduction inlet provided in the vicinity of the process cartridge unit.

The filter may include a catalyst for decomposing ozone.

The filter may include a deodorant filter using one of a catalyst and activated carbon.

The filter may include zeolite.

BRIEF DESCRIPTION OF THE DRAWINGS

A more complete appreciation of the invention and many of the advantages thereof may be obtained as the same becomes better understood by reference to the following detailed description when considered in connection with the accompanying drawings, wherein.

DETAILED DESCRIPTION OF PREFERRED EMBODIMENTS

In describing the embodiments illustrated in the drawings, specific terminology is employed for the purpose of clarity. However, the disclosure of this patent specification is not intended to be limited to the specific terminology so used, and it is to be understood that substitutions for each specific element can include any technical equivalents that operate in a similar manner and achieve a similar result.

Referring now to the drawings, embodiments of the present invention will be described. Throughout the following embodiments and modified examples thereof, like reference numerals designate identical or corresponding parts, such as members or components having the same function or shape, as long as the parts can be identified, and redundant description will be omitted.

Figure 2:
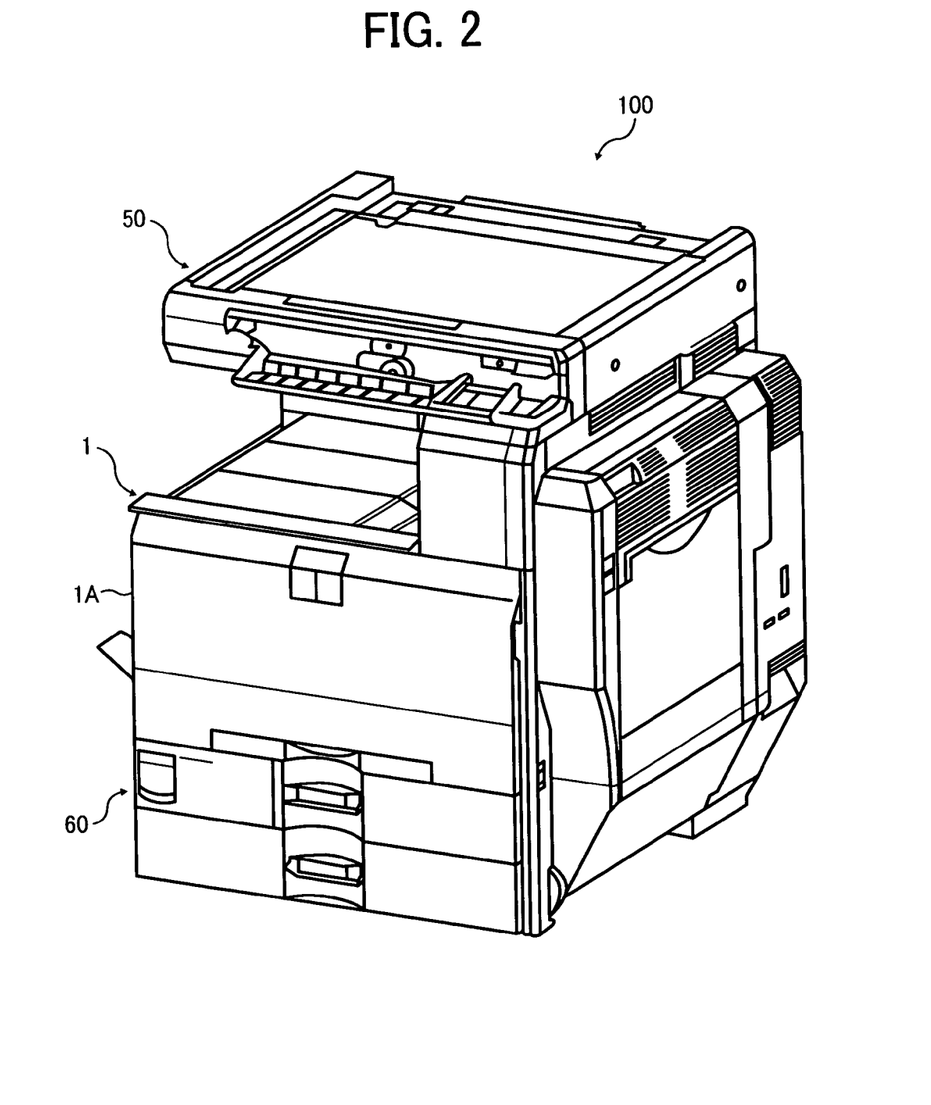
FIG. 2 is a perspective view illustrating an image forming apparatus according to an embodiment of the present invention.

FIG. 2 illustrates a schematic view of a full-color copier 100 as an image forming apparatus according to an embodiment of the present invention. In the image forming apparatus, an image reading unit 50 is provided in an upper part of an apparatus body 1, and a sheet feeding unit 60 is provided in a lower part of the apparatus body 1. The apparatus body 1 includes an external surface 1A.

Figure 3:
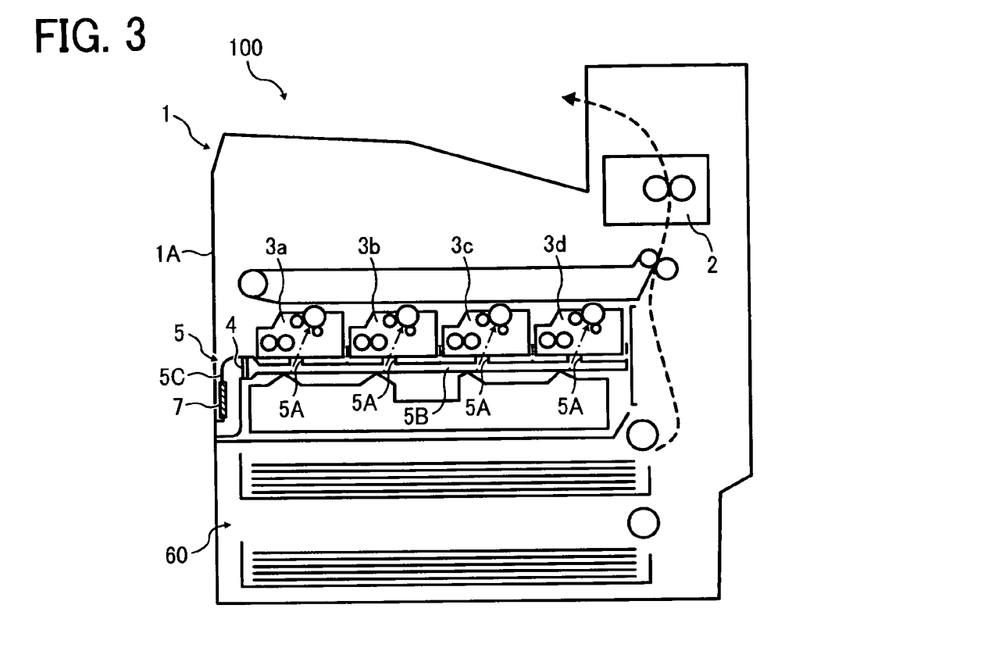
FIG. 3 is a diagram illustrating a schematic configuration of the interior of the image forming apparatus illustrated in FIG. 2.

As illustrated in FIG. 3, the apparatus body 1 stores a plurality of process cartridge units 3a, 3b, 3c, and 3d, a fixing unit 2, an exhaust fan 4, an exhaust duct 5, and a filter 7. The exhaust duct 5 includes a plurality of gas introduction inlets 5A, an exhaust path 5B, and a filter installation portion 5C. Each of the process cartridge units 3a, 3b, 3c, and 3d forms an image forming unit, which forms, on the basis of image information read by the image reading unit 50, a toner image to be transferred onto a sheet (i.e., recording medium) fed from the sheet feeding unit 60. The toner image transferred on the sheet is fixed thereon by the fixing unit 2. Each of the process cartridge units 3a, 3b, 3c, and 3d is a well-known process cartridge unit configured as a single unit including an image carrying member, a charging device, and a development device. The process cartridge units 3a, 3b, 3c, and 3d form yellow, cyan, magenta, and black toner images, respectively.

The fixing unit 2 is a well-known fixing unit that fixes toner transferred on a sheet by fusing the toner with pressure applied to the sheet at a relatively high temperature. In some cases, a chemical substance, such as an odorous substance, is volatilized from the toner during the heat treatment in the fixing process. Further, depending on the type of the charging device provided therein, such as the charging device using the corona discharge method, for example in some cases the process cartridge units 3a to 3d generate ozone in the charging of the image carrying member.

As illustrated in FIG. 3, therefore, the image forming apparatus includes the exhaust fan 4, the exhaust duct 5, and the filter 7. The exhaust duct 5 discharges the gas (air) in the apparatus body 1 to the outside thereof by using an airflow generated by the rotation of the exhaust fan 4. The filter 7 is provided in the pathway of the airflow flowing through the exhaust duct 5, and reduces a chemical substance contained in the gas in the apparatus body 1. The exhaust fan 4 and the exhaust duct 5, which discharge the gas in the apparatus body 1 to the outside thereof, also function as a cooling device that discharges the gas heated by the operation of the image forming apparatus.

The exhaust duct 5 includes the exhaust path 5B provided under the process cartridge units 3a to 3d in the apparatus body 1 and the filter installation portion 5C in which the filter 7 is installed. In the present embodiment, the exhaust path 5B includes the plurality of gas introduction inlets 5A respectively formed in the vicinity of the process cartridge units 3a to 3d. The present embodiment is configured such that, as the exhaust fan 4 rotates, ambient gas (air) around the process cartridge units 3a to 3d is suctioned through the gas introduction inlets 5A and flows through the exhaust path 5B.

The exhaust fan 4 is a well-known exhaust fan, which is rotated by a not-illustrated drive motor to generate, in the exhaust path 5B, a negative pressure and a resultant airflow flowing toward the filter installation portion 5C.

Figure 4:
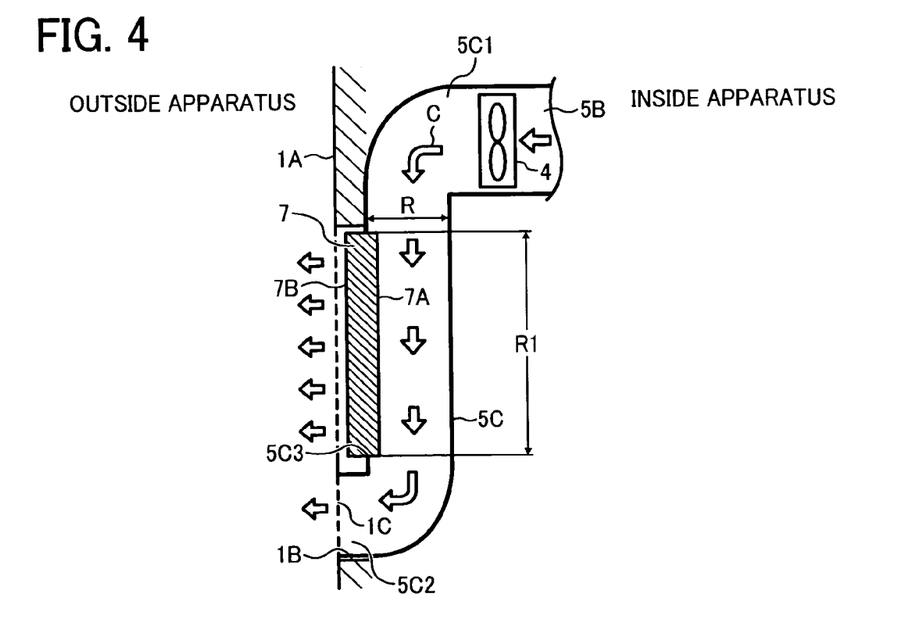
FIG. 4 is an enlarged view illustrating a configuration of the first embodiment of the present invention, wherein the area of a filter is set to be larger than the cross-sectional area of an exhaust duct.

As illustrated in FIG. 4, the filter installation portion 5C is provided on the exhaust path 5B, with one end opening portion 5C1 thereof communicating with the downstream side of the exhaust fan 4 in the ventilation direction, and the other end opening portion 5C2 thereof facing and communicating with an opening portion 1B formed in the external surface 1A of the apparatus body 1. In the present embodiment, the opening portion 1B, represented by a broken line, is not a fully open opening but is instead formed as slits 1C in the apparatus body. In the drawings, arrows C represent the airflow.

The filter installation portion 5C forming the exhaust duct 5 has a circular cross section. Herein, the cross-sectional area of the exhaust duct 5 is represented as R. The filter installation portion 5C includes an installation opening portion 5C3 which is formed in the pathway between the other end opening portion 5C2 and the exhaust fan 4, and in which the filter 7 is installed. Similarly to the other end opening portion 5C2, the installation opening portion 5C3 is also configured to face and communicate with the opening portion 1B.

The filter 7 of the present embodiment is a filter having an ozone purifying effect, and is installed in the installation opening portion 5C3 to be arranged parallel or substantially parallel to the ventilation direction of the exhaust duct 5. The filter 7 installed in the installation opening portion 5C3 is arranged such that one surface 7A thereof faces the interior of the exhaust path 5B and the other surface 7B thereof faces the opening portion 1B. In the present embodiment, the contact area of the filter 7 in the exhaust path 5B exposed to the airflow flowing through the exhaust path 5B, represented as R1, is larger than a cross-sectional area R of the exhaust duct 5. Further, the filter 7 is provided in the vicinity of the external surface 1A of the apparatus body 1 such that the external surface 1A and the other surface 7B are parallel or substantially parallel to each other.

According to the thus-configured image forming apparatus, when an airflow is generated in the exhaust path 5B in accordance with the rotation of the exhaust fan 4, the ambient gas (air) around the process cartridge units 3a to 3d is suctioned through the gas introduction inlets 5A, flows through the exhaust path 5B, and passes the filter 7 in the filter installation portion 5C. Thereby, the airflow with purified ozone and reduced odor is discharged outside the apparatus body 1 through the opening portion 1B of, the apparatus body 1.

By contrast, in the background example described above, the filter is arranged perpendicular to the exhaust path. Therefore, the resistance in the filter caused by the ozone-containing airflow passing through the filter is relatively large, and thus causes pressure loss. However, in the present embodiment, the filter 7 is arranged parallel or substantially parallel to the ventilation direction of the exhaust duct 5, and the area R1 of the filter 7 exposed to the airflow in the exhaust path 5B is set to be larger than the cross-sectional area R of the exhaust duct 5. In the present embodiment, therefore, the wind velocity of the airflow passing through the filter 7 is reduced below that of the configuration including the filter arranged perpendicular to the exhaust path as in the background example. Further, the portion installed with the filter 7 is provided separately from the other end opening portion 5C2. Therefore, the flow resistance against the airflow flowing through the exhaust path 5B is reduced. As a result, a load on the exhaust fan 4 is reduced, and cooling performance is improved.

Further, with the filter 7 arranged parallel or substantially parallel to the ventilation direction of the exhaust duct 5, the wind velocity of the airflow passing through the filter 7 is equalized. More specifically, as described above in the background example of FIG. 1, if the filter is arranged perpendicular to the ventilation direction of the exhaust duct, the influence of fan wind (i.e., dynamic pressure) generated by the exhaust fan on the air passing through the filter is relatively large, and thus the wind velocity of the airflow passing through the filter tends to vary due to uneven impact of the wind on the filter. By contrast, with the filter 7 arranged parallel or substantially parallel to the ventilation direction of the exhaust duct 5 as in the present embodiment, the influence of an increase in air pressure in the space between the exhaust fan 4 and the filter 7 (i.e., static pressure) is increased, and the wind velocity of the airflow passing through the filter 7 is equalized. In the present embodiment, therefore, the pressure loss at the filter 7 is less than in the configuration of the background example, and there is no need to increase the output of the exhaust fan 4. Accordingly, necessary and sufficient odor reduction can be performed with relatively low noise and power consumption, and the cooling performance can be ensured.

With the filter 7 arranged in the vicinity of and parallel or substantially parallel to the external surface 1A of the apparatus body 1, a reduction in required space can be achieved, even if the filter 7 is increased in size with the length thereof increased in the ventilation direction. Further, with this configuration, a better odor reducing effect can be obtained.

Figure 5:
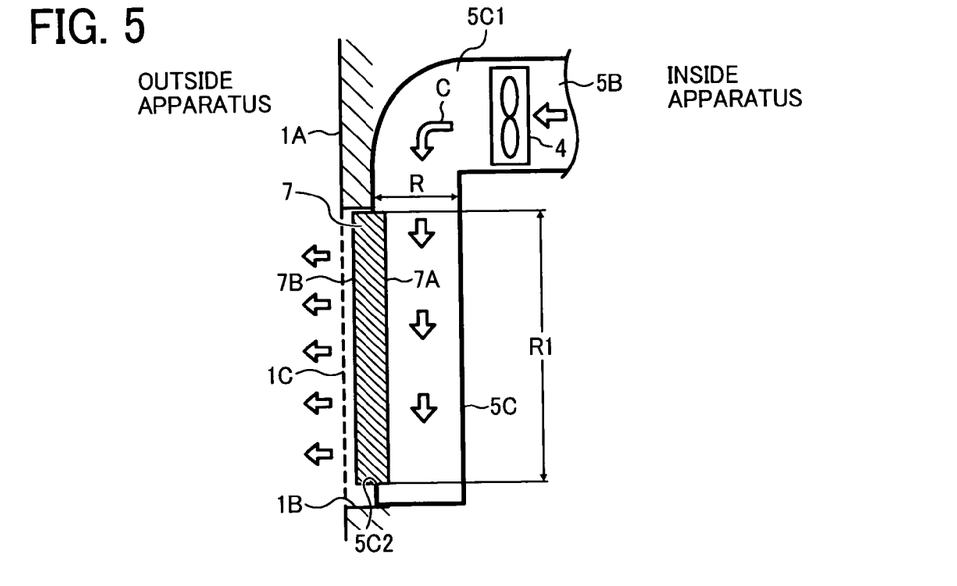
FIG. 5 is an enlarged view illustrating a configuration of a second embodiment of the present invention.

FIG. 5 illustrates a second embodiment of the present invention. In the present embodiment, the installation opening portion 5C3 is not formed in the filter installation portion 5C, and the filter 7 is arranged in the other end opening portion 5C2 of the filter installation portion 5C. In the present embodiment, therefore, the length of the filter 7 in the ventilation direction can be set to be longer than in the embodiment of FIG. 4. Also in this case, the filter 7 is arranged parallel or substantially parallel to the ventilation direction of the exhaust duct 5, and the area R1 of the filter 7 exposed to the airflow in the exhaust path 5B is set to be larger than the cross-sectional area R of the exhaust duct 5.

According to the configuration, the pressure loss at the filter 7 is less than in the configuration of the background example, and there is no need to increase the output of the exhaust fan 4. Therefore, necessary and sufficient odor reduction can be performed with relatively low noise and power consumption, and the cooling performance can be ensured. Further, the area R1 of the filter 7 can be set to be larger than in the embodiment illustrated in FIG. 4. Therefore, a better odor reducing effect can be obtained.

Figure 6:
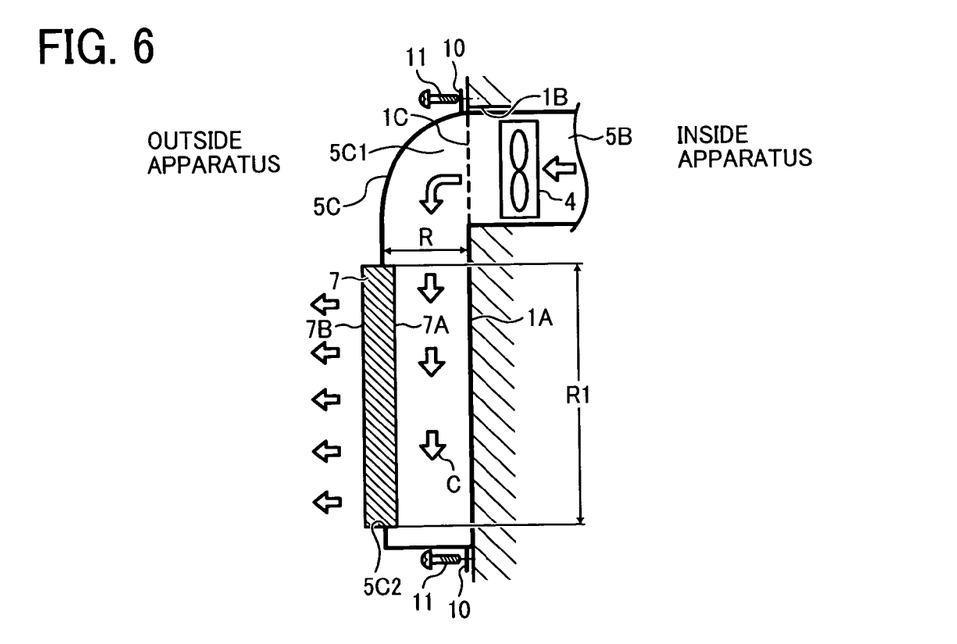
FIG. 6 is an enlarged view illustrating a configuration of a third embodiment of the present invention, wherein a filter installation portion is provided outside an apparatus body.

FIG. 6 illustrates a third embodiment of the present invention. In the present embodiment, the filter installation portion 5C including the filter 7 illustrated in FIG. 5 is provided outside the external surface 1A of the apparatus body 1 to be detachably attachable to the external surface 1A. In this case, an installation flange 10 is formed around the outer circumference of the filter installation portion 5C and fixed to the external surface 1A with one or a plurality of screws 11, with one end opening portion 5C1 of the filter instillation portion 5C facing the opening portion 1B of the apparatus body 1.

The filter installation portion 5C including the filter 7 is thus provided in the vicinity of the opening portion 1B to be detachably attachable to the external surface 1A. Therefore, the filter installation portion 5C can be provided to the image forming apparatus in accordance with the request of the user, and thus odor reduction according to the preference of the user can be achieved. In the present embodiment, the filter 7 can also be exposed to the outside of the apparatus body 1. If the filter 7 is configured to be attachable to and detachable from the filter installation portion 5C, therefore, the filter replacement operation can be performed with relative ease. If the filter 7 and the filter installation portion 5C are integrated with each other, the filter installation portion 5C can be replaced with relative ease by a spare filter installation portion 5C including a different type (e.g., different function) of filter 7, with the screws 11 removed therefrom. Thereby, odor reduction more suited to the preference of the user can be achieved.

Figure 7:
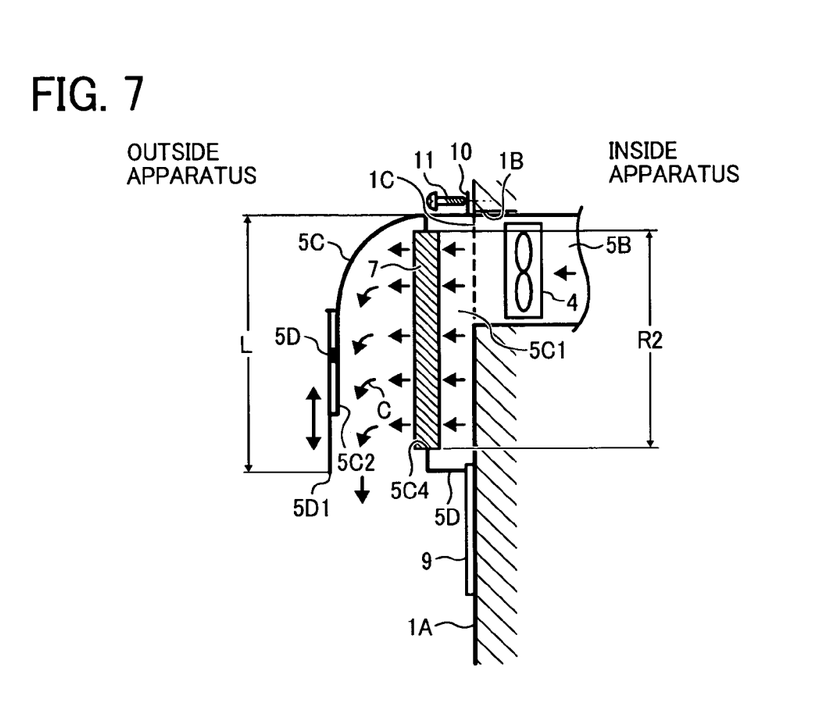
FIG. 7 is an enlarged view illustrating a configuration of a fourth embodiment of the present invention, wherein an opening of the filter installation portion has a variable area.
Figure 8:
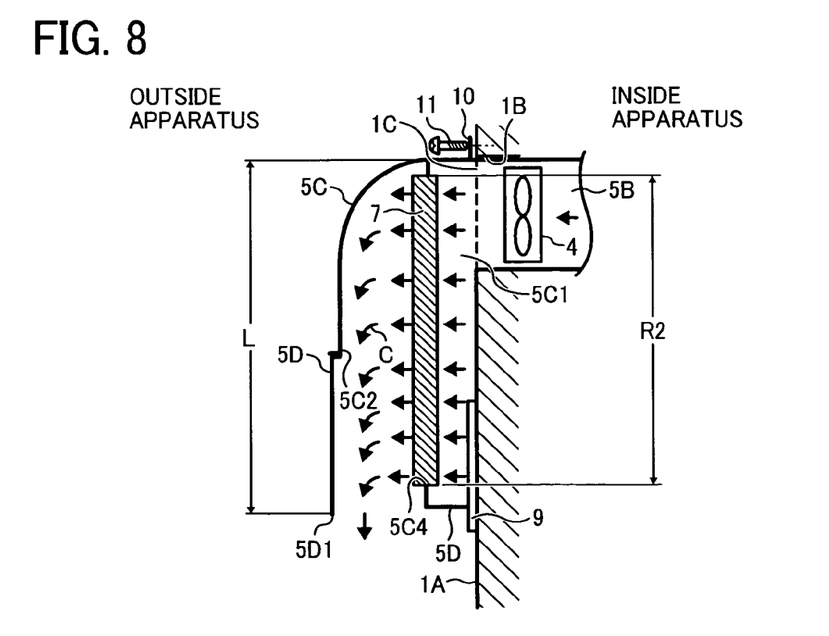
FIG. 8 is an enlarged view illustrating a state in which the opening of the filter installation portion illustrated in FIG. 7 is increased.

FIGS. 7 and 8 illustrate a fourth embodiment of the present invention. In the present embodiment, when R2 represents an opening of the filter installation portion 5C installed with the filter 7, i.e., an opening of an installation opening portion 5C4, the opening R2 is set to be variable.

A structure capable of changing the opening R2 includes a movable portion 5D which is movable with respect to the filter installation portion 5C, which is a fixed portion. The installation flange 10 is formed around the outer circumference of the filter installation portion 5C as a fixed portion. The filter installation portion 5C is provided outside the apparatus body 1. With the one end opening portion 5C1 of the filter installation portion 5C facing the opening portion 1B of the apparatus body 1, the installation flange 10 is fixed to the external surface 1A with one or a plurality of screws 11.

The movable portion 5D has a cylindrical shape for covering the outer surface of the filter installation portion 5C, and a part thereof is fixed to a slider 9 attached to the apparatus body 1 such that the movable portion 5D can move in the directions of expansion and contraction with respect to the filter installation portion 5C. The present embodiment is configured such that the installation opening portion 5C4 installed with the filter 7 is formed between the filter installation portion 5C and the movable portion 5D, and that the opening R2 of the installation opening portion 5C4 changes in accordance with the movement of the movable portion 5D in the directions of expansion and contraction with respect to the filter installation portion 5C as a fixed portion. FIG. 7 illustrates a state in which the movable portion 5D is stored in the filter installation portion 5C as a fixed portion, and FIG. 8 illustrates a state in which the movable portion 5D projects and extends from the filter installation portion 5C.

This configuration allows the opening R2 of the installation opening portion 5C4 of the filter installation portion 5C to be freely changed in accordance with the movement of the movable portion 5D. Thus, the opening R2 can be arbitrarily changed in accordance with the size of the filter 7. Therefore, the filter 7 and the size thereof can be selected in accordance with the usage of the image forming apparatus in the market or the preference of the user. Accordingly, odor reduction according to the preference of the user or the usage can be achieved. Further, as illustrated in FIGS. 7 and 8, it is possible to change the total length L from the filter installation portion 5C to a leading end 5D1 of the movable portion 5D by moving the movable portion 5D. Therefore, the exhaust duct 5 can be installed in an appropriate layout fit to the size of the filter 7. Further, the variable structure of the exhaust duct 5 according to the present embodiment allows the opening R2 to be changed by a relatively simple configuration which moves the movable portion 5D with respect to the filter installation portion 5C as a fixed portion. Accordingly, a reduction in cost can be achieved.

Figure 9:
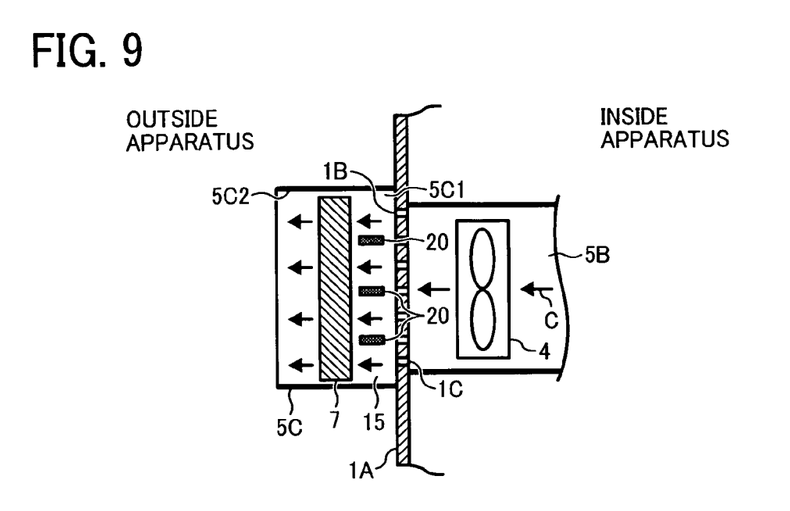
FIG. 9 is an enlarged view illustrating a configuration of a fifth embodiment of the present invention, wherein wind rectification ribs are provided in a pathway space located between an exhaust fan and the filter.

FIG. 9 illustrates a fifth embodiment of the present invention. In the present embodiment, a plurality of wind rectification ribs 20 are provided in a pathway space 15 located between the exhaust fan 4 and the filter 7. In the example illustrated in FIG. 9, the filter installation portion 5C installed with the filter 7 is provided outside the apparatus body 1. Therefore, the pathway space 15 is located inside the filter installation portion 5C, and the plurality of wind rectification ribs 20 are also formed inside the filter installation portion 5C. The wind rectification ribs 20 can be provided in any location, as long as the location is inside the pathway space 15 located between the exhaust fan 4 and the filter 7. For example, therefore, the wind rectification ribs 20 may be provided on the external surface 1A of the apparatus body 1.

With the wind rectification ribs 20 thus provided in the pathway space 15 located between the exhaust fan 4 and the filter 7, the pressure loss is reduced in the space between the exhaust fan 4 and the filter 7, which tends to act as a bottleneck for the airflow. Therefore, there is no need to increase the output of the exhaust fan 4. Accordingly, necessary and sufficient odor reduction can be performed with relatively low noise and power consumption, and the cooling performance can be ensured.

Figure 10:
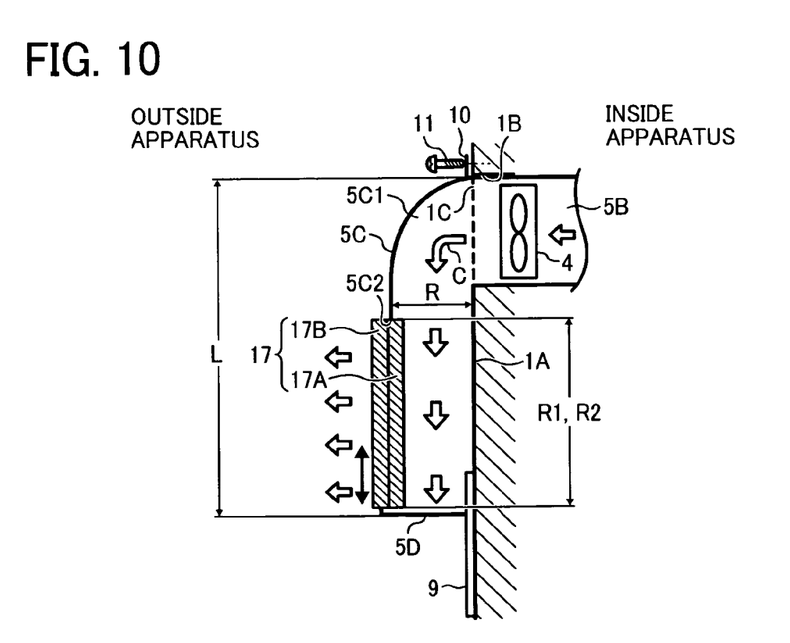
FIG. 10 is an enlarged view illustrating a configuration of a sixth embodiment of the present invention, wherein the area of a filter is set to be larger than the cross-sectional area of the exhaust duct and the opening of the filter installation portion has a variable area.
Figure 11:
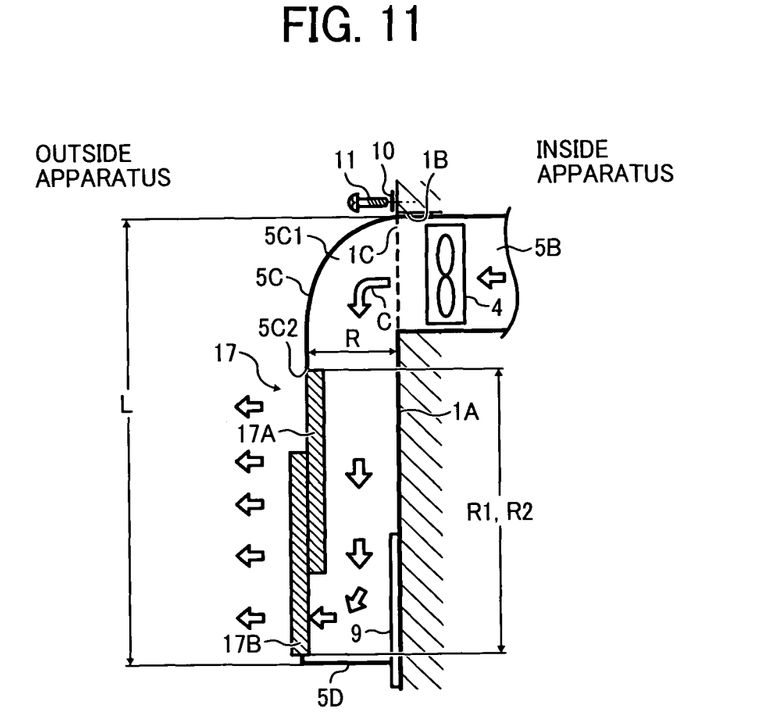
FIG. 11 is an enlarged view illustrating a state in which the opening of the filter installation portion illustrated in FIG. 10 is increased.

FIGS. 10 and 11 illustrate a sixth embodiment of the present invention. The present embodiment includes the third embodiment illustrated in FIG. 6 and the fourth embodiment illustrated in FIGS. 7 and 8. That is, in FIGS. 10 and 11, the filter installation portion 5C as a fixed portion and the movable portion 5D form the other end opening portion 5C2 serving as the installation opening portion, and the other end opening portion 5C2 is provided with a movable filter 17.

The filter 17 is arranged parallel or substantially parallel to the ventilation direction of the airflow flowing through the filter installation portion 5C. Further, the contact area R1 of the filter 17 exposed to the airflow flowing through the filter installation portion 5C is formed to be larger than the cross-sectional area R of the exhaust duct 5. The filter 17 is configured to include a fixed filter 17A and a movable filter 17B supported to be slidable with respect to the fixed filter 17A. The fixed filter 17A is fixed to the filter installation portion 5C forming one side of the other end opening portion 5C2. The movable portion 5D forming the other side of the other end opening portion 5C2 has one end fixed to the slider 9 and the other end fixed to the movable filter 17B. FIG. 10 illustrates the stored state of the movable portion 5D, and FIG. 11 illustrates the projected state of the movable portion 5D, in which the opening R2 and the area R1 of the filter 17 are increased.

According to the configuration, the opening R2 of the other end opening portion 5C2 of the filter installation portion 5C can be freely changed in accordance with the movement of the movable portion 5D. Further, the movable filter 17B also moves in conjunction with the movement of the movable portion 5D. It is therefore possible to increase or reduce the contact area R1 of the filter 17 exposed to the airflow. Further, the contact area R1 of the filter 17 is formed to be larger than the cross-sectional area R even in the shortest state of the filter 17 illustrated in FIG. 10, in which the movable portion 5D is stored and the fixed filter 17A and the movable filter 17B are superimposed on each other. Therefore, the filter 17 and the size thereof can be selected in accordance with the usage of the image forming apparatus in the market or the preference of the user. Accordingly, odor reduction according to the preference of the user or the usage can be achieved. Further, in the present configuration, the wind velocity of the airflow passing through the filter 17 is reduced to be lower than in the configuration including the filter arranged perpendicular to the exhaust path, as in the background example. Further, with the filter 17 arranged parallel or substantially parallel to the ventilation direction of the exhaust duct 5, the wind velocity of the airflow passing through the filter 17 is equalized. In the present configuration, therefore, the pressure loss at the filter 17 is less than in the configuration of the background example, and there is no need to increase the output of the exhaust fan 4. Accordingly, necessary and sufficient odor reduction can be performed with relatively low noise and power consumption, and the cooling performance can be ensured. Further, it is possible to change the total length L from the filter installation portion 5C to the leading end 5D1 of the movable portion 5D. Therefore, the exhaust duct 5 can be installed in an appropriate layout fit to the size of the filter 17. Further, the variable structure of the exhaust duct 5 according to the present embodiment allows the contact area R1 of the filter 17 and the opening R2 to be changed by a relatively simple configuration which moves the movable portion 5D with respect to the filter installation portion 5C as a fixed portion. Accordingly, a reduction in cost can be achieved.

The movable portion 5D illustrated in FIGS. 7 and 8 and FIGS. 10 and 11 is provided downstream of the filter 7 or 17 in the ventilation direction, and has a cover shape for guiding the airflow having passed the filter 7 or 17 toward the lower side of the apparatus body 1. It is therefore possible to discharge the airflow purified by the filter 7 or 17 toward the lower side of the apparatus body 1, and thus to prevent the user from being exposed to the exhaust wind.

The above-described embodiments reduce ozone as a chemical substance generated from the process cartridge units 3a to 3d. Meanwhile, if the process cartridge units 3a to 3d do not include a charging device using a method which turns the charging device into a source of ozone, the gas introduction inlets 5A of the exhaust duct 5 may be provided in the vicinity of the fixing unit 2 to reduce an odorous substance generated from the fixing unit 2 in the fixing process. Further, a deodorant filter using a catalyst or activated carbon or a filter using zeolite, for example, may be used as the filter 7 or 17. With this configuration, it is possible to reduce the odorous substance volatilized from the toner in the fixing process, which is contained in the gas in the apparatus body 1.

It is needless to say that, irrespective of the type of the charging device, the gas introduction inlets 5A of the exhaust duct 5 may be provided in the vicinity of the fixing unit 2 to reduce the odorous substance volatilized from the toner in the fixing process. Further, the gas introduction inlets 5A may be provided in the vicinity of the process cartridge units 3a to 3d and in the vicinity of the fixing unit 2 such that ozone generated from the process cartridge units 3a to 3d and the odorous substance volatilized from the toner in the fixing process are both purified at one time.

The image forming apparatus according to an embodiment of the present invention is not limited to the color copier 100, and may be a facsimile machine, a printer, or a so-called multifunctional machine having the image forming function and other functions. Further, the image forming apparatus may be a monochrome image forming apparatus.

In the above-described embodiments, the screws 11 are used to install the filter installation portion 5C to the external surface 1A to be attachable thereto and detachable therefrom. Alternatively, the screws 11 may be replaced by, for example, a double-sided adhesive tape to install the filter installation portion 5C to a portion of the external surface 1A surrounding the opening portion 1B to be attachable thereto and detachable therefrom.

When the combination of the filter 7 and the filter installation portion 5C holding the filter 7 or the combination of the filter 7 or 17, the filter installation portion 5C holding the filter 7 or 17, and the movable portion 5D form a duct device, the field of application of the duct device is not limited to the image forming apparatus. If the duct device is installed in an opening portion serving as an exhaust port of an apparatus for discharging a gas containing a chemical substance and/or an odorous substance, there is no need to increase the output of the exhaust fan 4, and necessary and sufficient odor reduction can be performed with relatively low noise and power consumption.

The above-described embodiments are illustrative and do not limit the present invention. Thus, numerous additional modifications and variations are possible in light of the above teachings. For example, elements at least one of features of different illustrative and exemplary embodiments herein may be combined with each other at least one of substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of this patent specification may be practiced otherwise than as specifically described herein.

The invention claimed is:

1. An image forming apparatus, comprising:
    an exhaust fan;
    an exhaust duct to discharge a gas in an apparatus body to the outside thereof by using an airflow generated by the rotation of the exhaust fan; and
    a filter provided in a pathway of an airflow flowing through the exhaust duct, the entire filter being arranged substantially parallel to a ventilation direction of the exhaust duct, to reduce chemical substances contained in the gas.

2. The image forming apparatus according to claim 1, wherein an area of the filter exposed to the airflow in the pathway is larger than a cross-sectional area of the exhaust duct.

3. The image forming apparatus according to claim 1, wherein the filter is substantially parallel to an external surface of the apparatus body.

4. The image forming apparatus according to claim 1, further comprising:
    a wind rectification rib provided in a pathway space located between the exhaust fan and the filter.

5. The image forming apparatus according to claim 1, further comprising a fixing unit provided in the apparatus body.

6. The image forming apparatus according to claim 1, further comprising a process cartridge unit provided in the apparatus body,
    wherein the exhaust duct includes a gas introduction inlet, the gas introduction inlet being configured to pass gas from around the process cartridge unit to an exhaust path connected to the exhaust duct.

7. The image forming apparatus according to claim 1, wherein the filter includes a catalyst for decomposing ozone.

8. The image forming apparatus according to claim 1, wherein the filter includes a deodorant filter using one of a catalyst and activated carbon.

9. The image forming apparatus according to claim 1, wherein the filter includes zeolite.

10. An image forming apparatus, comprising:
    an exhaust fan;
    an exhaust duct to discharge a gas in an apparatus body to the outside thereof by using an airflow generated by the rotation of the exhaust fan; and
    a filter provided in a pathway of an airflow flowing through the exhaust duct, arranged substantially parallel to a ventilation direction of the exhaust duct, to reduce chemical substances contained in the gas; wherein
        the exhaust duct includes a filter installation portion in which the filter is installed, and which is located outside an external surface of the apparatus body and detachably attachable to the external surface.

11. The image forming apparatus according to claim 10, wherein an opening of the filter installation portion has a variable area.

12. The image forming apparatus according to claim 11, wherein the exhaust duct includes a fixed portion and a movable portion which is movable with respect to the fixed portion, and which is moved to change the opening.

13. An image forming apparatus, comprising:
    an exhaust fan;
    an exhaust duct to discharge a gas in an apparatus body to the outside thereof by using an airflow generated by rotation of the exhaust fan; and
    a filter in a pathway of airflow through the exhaust duct, the filter being arranged substantially parallel to a ventilation direction of at least a portion of the exhaust duct to reduce chemical substances contained in the gas; wherein
        the exhaust duct includes a filter installation portion in which the filter is installed, and
        an opening of the filter installation portion has a variable area.

14. The image forming apparatus according to claim 13, wherein the exhaust duct includes a movable portion configured to move with respect to the filter installation portion to vary the area of the opening.

* * * * *